US010213376B2

(12) United States Patent
Takagi et al.

(10) Patent No.: US 10,213,376 B2
(45) Date of Patent: Feb. 26, 2019

(54) METHOD OF SUPPRESSING COLORATION OF CATECHINS AND A DENTIFRICE COMPOSITION

(71) Applicant: Kao Corporation, Chuo-ku (JP)

(72) Inventors: Michiya Takagi, Wakayama (JP); Satoshi Ueno, Wakayama (JP); Koji Mine, Wakayama (JP); Hideaki Kubo, Wakayama (JP); Ikuhisa Ichimura, Tokyo (JP); Gen Nakauchi, Tokyo (JP); Kazushi Oshino, Tokyo (JP)

(73) Assignee: KAO CORPORATION, Tokyo (JP)

( * ) Notice: Subject to any disclaimer, the term of this patent is extended or adjusted under 35 U.S.C. 154(b) by 350 days.

(21) Appl. No.: 14/680,145

(22) Filed: Apr. 7, 2015

(65) Prior Publication Data

US 2015/0209267 A1    Jul. 30, 2015

Related U.S. Application Data

(62) Division of application No. 12/374,099, filed as application No. PCT/JP2007/063202 on Jun. 26, 2007, now abandoned.

(30) Foreign Application Priority Data

Jul. 21, 2006  (JP) ................. 2006-199515
Jul. 21, 2006  (JP) ................. 2006-199516

(51) Int. Cl.
| | | |
|---|---|---|
| *A61K 8/34* | (2006.01) | |
| *A61K 8/81* | (2006.01) | |
| *A61K 8/04* | (2006.01) | |
| *A61K 31/353* | (2006.01) | |
| *A61Q 11/00* | (2006.01) | |
| *C07D 311/62* | (2006.01) | |
| *C08K 5/1545* | (2006.01) | |
| *A61K 8/49* | (2006.01) | |
| *A61K 8/73* | (2006.01) | |

(52) U.S. Cl.
CPC ............ *A61K 8/8176* (2013.01); *A61K 8/042* (2013.01); *A61K 8/347* (2013.01); *A61K 8/498* (2013.01); *A61K 8/73* (2013.01); *A61K 8/731* (2013.01); *A61K 8/8182* (2013.01); *A61K 31/353* (2013.01); *A61Q 11/00* (2013.01); *C07D 311/62* (2013.01); *C08K 5/1545* (2013.01); *A61K 2800/41* (2013.01); *A61K 2800/54* (2013.01); *A61K 2800/805* (2013.01)

(58) Field of Classification Search
CPC ...... A61K 8/8176; A61K 8/042; A61K 8/347; A61K 8/498; A61K 8/73; A61K 8/731; A61K 8/8182; A61K 31/353; A61K 2800/41; A61K 2800/54; A61K 2800/805; C08K 5/1545; A61Q 11/00; C07D 311/62
USPC ........................................................ 424/49
See application file for complete search history.

(56) References Cited

U.S. PATENT DOCUMENTS

| | | |
|---|---|---|
| 4,935,256 A | 6/1990 | Tsai |
| 5,961,990 A | 10/1999 | Delrieu et al. |
| 2001/0002252 A1* | 5/2001 | Gallopo .............. A61K 8/22 424/49 |
| 2002/0034525 A1 | 3/2002 | Sakai et al. |
| 2004/0062835 A1 | 4/2004 | Earl et al. |
| 2006/0024416 A1 | 2/2006 | Casper et al. |
| 2006/0140881 A1* | 6/2006 | Xu .................... A61K 8/345 424/49 |
| 2006/0141072 A1 | 6/2006 | Arvanitidou et al. |
| 2006/0264497 A1 | 11/2006 | Zeligs |
| 2007/0184105 A1 | 8/2007 | Kim et al. |
| 2011/0165099 A1 | 7/2011 | Arvanitidou et al. |

FOREIGN PATENT DOCUMENTS

| | | |
|---|---|---|
| FR | 2 773 811 | 7/1999 |
| JP | 61-225115 | 10/1986 |
| JP | 1-90124 | 4/1989 |
| JP | 1-218550 | 8/1989 |
| JP | 1-275520 | 11/1989 |
| JP | 2-25413 | 1/1990 |
| JP | 3-86814 | 4/1991 |
| JP | 6-239716 | 8/1994 |
| JP | 8-333380 | 12/1996 |
| JP | 9-47654 | 2/1997 |
| JP | 2000-297022 | 10/2000 |
| JP | 2001-288074 | 10/2001 |
| JP | 2003-503324 | 1/2003 |
| WO | 98/50000 | 11/1998 |

(Continued)

OTHER PUBLICATIONS

Extended Search Report dated Jun. 11, 2012 in European Application No. 07767980.1.
Office Action dated Jan. 31, 2012, in Chinese Patent Application No. 200780027748.9 filed Jun. 26, 2007 (with English translation).
Office Action dated Sep. 15, 2011, in Chinese Patent Application No. 200780027748.9 (English translation only).
N. Kamiyama, "Yakon Kaikon no Kappen Boshiho", Shikoku Nogyo Kenkyu Seika Joho, vol. 2000, pp. 196-197(Dec. 31, 2001)(with partial English translation).
Chinese Office Action dated Feb. 24, 2011 in corresponding Chinese Application No. 200780027748.9 (with an English translation).

(Continued)

*Primary Examiner* — Adam C Milligan

(74) *Attorney, Agent, or Firm* — Oblon, McClelland, Maier & Neustadt, L.L.P.

(57) ABSTRACT

The present invention relates to a method of suppressing coloration of catechins, which contains adding, to catechins, a water-soluble polymer forming a water-insoluble complex with catechins, as well as hydrogel particles containing a water-insoluble complex between catechins and a polymer forming a water-insoluble complex with catechins. Further, the present invention relates to a dentifrice composition containing hydrogel particles containing catechins and a polymer forming a water-insoluble complex with catechins, a binder and water.

14 Claims, 2 Drawing Sheets

(56) References Cited

FOREIGN PATENT DOCUMENTS

| WO | 2005/049704 A1 | 6/2005 |
| WO | 2005-068210 | 7/2005 |
| WO | 2005/087224 A1 | 9/2005 |
| WO | 2006/105196 A2 | 10/2006 |

OTHER PUBLICATIONS

Baron, et al., "Comparative Study of Browning and Flavan-3-Ols during the Storage of White Sherry Wines Treated with Different Fining Agents", Journal of the Science of Food and Agriculture, vol. 80, No. 2, pp. 226-230 (2000).

McMurrough, et al., "Effect of the Removal of Sensitive Proteins and Proanthocyanidins on the Colloidal Stability of Lager Beer", Journal of the American Society of Brewing Chemists, vol. 50, No. 2, pp. 67-76 (1992).

Chen, et al., "Effects of Different Clarification Methods on Polyphenol Content and Turbidity of Jasmine Tea Extract and Diluted Jasmine Tea Infusion", Food Science, vol. 26, No. 3, pp. 315-329 (1999).

Spagna, et al., "The Stabilization of White Wines by Adsorption of Phenolic Compounds on Chitin and Chitosan", Food Research International, vol. 29, No. 3-4, pp. 241-248 (1996).

R. Binning, "Light Colour-Stable Cloudy Apple Juices", Confructa Studien, vol. 36, No. 3/4, pp. 92-97 (1992).

\* cited by examiner

METHOD OF SUPPRESSING COLORATION OF CATECHINS AND A DENTIFRICE COMPOSITION

This application is a divisional of U.S. application Ser. No. 12/374,099 filed Mar. 24, 2009, which is a National Stage of PCT/JP2007/063202 filed Jun. 26, 2007, both of which are incorporated herein by reference. This application also claims the benefit of JP 2006-199515 filed Jul. 21, 2006 and JP 2006-199516 filed Jul. 21, 2006.

FIELD OF THE INTENTION

The present invention relates to a method of suppressing coloration of catechins and hydrogel particles containing a water-insoluble complex of catechins. The present invention also relates to a dentifrice composition containing catechins.

BACKGROUND OF THE INVENTION

Catechin, tannin, etc. are known as polyphenols contained in tea leaves. Particularly, catechins are known to have various physiological functions such as antioxidative action, antibacterial action, blood cholesterol-level-rise suppressive action, blood-pressure-rise suppressive action and blood-sugar-level-rise inhibitory action. However, catechins themselves are potent antioxidants and thus have a problem of undergoing oxidization and polymerization during storage. Further, catechins have a problem of discoloration upon oxidation and/or polymerization, thus restricting the degree of freedom of their application to pharmaceutical preparations. Accordingly, there is demand for a method of suppressing oxidation and polymerization of catechins.

JP-A 9-47654 relates to removal of polyphenols since the presence of excessive polyphenols in products deteriorates the commodity value, and is thus different in purpose from a method of suppressing oxidation and polymerization of catechins.

JP-A 8-333380 discloses a process for producing tea saponin, wherein an extract extracted with a water-containing lower alcohol from hot-water extraction residues of tea leaves is treated with water-insoluble polyvinyl pyrrolidone, thereby removing catechins from the extract.

JP-A 1-218550 discloses a process for producing tannin-free tea, which contains adding insoluble polyvinyl pyrrolidone to a filtered extract extracted with hot water, etc. from anaerobically treated tea leaves, and then filtering the extract.

It is known that dental caries and periodontitis are caused by dental bacteria. Accordingly, dental caries and periodontitis are prevented generally by killing dental bacteria or suppressing their activity with a dental composition compounded with a bacteriocide. Particularly with increasing natural-product orientation in recent years, a naturally derived component is used as the bacteriocide to avoid use of a chemically synthesized substance. For example, a green tea extract and its components that are tea polyphenol compounds (catechins etc.) are known to be effective in suppressing proliferation of dental bacteria (for example, JP-A 1-90124, JP-A 2-25413, JP-A 3-86814, etc.). These literatures describe that since green tea extracts, etc. prevent proliferation of *Stereptococcus mutans* that is a bacterium causing dental caries and *Porphyromonas gingivalis* that is a bacterium causing periodontitis, they can provide oral compositions effective in preventing dental caries and periodontitis. However, the polyphenol compounds (catechins etc.), when contacted with oxygen, undergo oxidation and polymerization to discolor significantly, so the discoloration with time of the oral composition itself compounded therewith is inevitable. As the method of suppressing such discoloration, for example, a method which contains incorporating sugar alcohols having 4 to 5 carbon atoms (for example, xylitol, erythritol etc.) into a polyphenol-containing plant extract and sealing the product in individual oxygen-impermeable bags is proposed (JP-A 2000-297022).

Meanwhile, as a method of incorporating various drugs, easily denatured active ingredients, and the like, into oral compositions, a method which contains stabilizing the ingredients by capsulating them or including them in shells etc. is also proposed (JP-A 61-225115, JP-A 1-275520, etc.).

SUMMARY OF THE INVENTION

The present invention provides a method of suppressing coloration of catechins, which includes adding, to catechins, a water-soluble polymer (referred to hereinafter as polymer A) capable of forming a water-insoluble complex with catechins.

The present invention also provides hydrogel particles containing a water-insoluble complex of catechins and polymer A.

Further, the present invention provides a dentifrice composition containing hydrogel particles containing catechin and a water-soluble polymer forming a water-insoluble complex with catechin, a binder and water.

The present invention provides use of a water-soluble polymer forming a water-insoluble complex with catechin in suppressing coloration of catechin. Further, the present invention provides dentifrice use of a composition containing hydrogel particles containing catechin and a water-soluble polymer forming a water-insoluble complex with catechin, a binder and water.

DETAILED DESCRIPTION OF THE INVENTION

JP-A 9-47654 discloses a polyphenol adsorbent containing a composite material containing an insoluble polyvinyl pyrrolidone contained in a base material of regenerated cellulose substance.

JP-A 8-333380 relates to removal of catechins, etc. that are unnecessary substances other than the objective substance saponin and is different in purpose from a method of suppressing oxidation and polymerization of catechins.

JP-A 1-218550 relates to removal of tannin components in an extract and is different in purpose from a method of suppressing oxidation and polymerization of catechins.

In the conventional technique, techniques of adsorptive removal of catechins by adsorbing the catechins onto polyvinyl pyrrolidone are known, but a method of preventing discoloration of catechins by suppressing oxidation and/or polymerization of the catechins is not known.

The present invention provides a method of preventing discoloration of catechins by suppressing coloration thereof, as well as hydrogel particles of catechins whose coloration is suppressed.

The inventors found that when hydrogel particles in which catechins and a specific polymer forming a water-insoluble complex with catechins have been included is contained in a dentifrice composition, it is possible to obtain a dentifrice composition excellent in sense of use wherein catechins are stably maintained while gel-like particles are easily destroyed by brushing to permit catechins to effectively act in the vicinity of the surfaces of teeth and gum.

The present invention provides a dentifrice composition excellent in sense of use wherein catechins are stably maintained, and when used, the catechins act effectively on teeth and gum.

According to the present invention, catechins can be stabilized by forming a water-insoluble complex with polymer A, thereby suppressing coloration of the catechins.

The dentifrice composition of the present invention maintains catechins stably, permits catechins to act effectively in the vicinity of the surfaces of teeth and gum, to improve the state of teeth and gum, and is excellent in sense of use.

In the present invention, catechins are non-polymer catechins and include, for example, non-epicatechins such as catechin, gallocatechin, catechingallate and gallocatechingallate, and epicatechins such as epicatechin, epigallocatechin, epicatechingallate and epigallocatechingallate. Catechins can be obtained by concentration, purification, etc. of a green tea extract extracted from tea leaves with hot water or a water-soluble organic solvent. Alternatively, commercially available green tea extract concentrates such as "Polyphenon" available from Mitsui Norin Co., Ltd, "Thea-furan" from Ito En, Ltd., and "Sunphenon" from Taiyo Kagaku Co., Ltd. can be used and subjected to regulation of components, thereby yielding green tea extracts serving the purpose of the present invention.

The polymer A used in the present invention is not particularly limited as long as it is a water-soluble polymer forming a water-insoluble complex with catechins.

The water-insoluble complex refers to a substance precipitated from water as insoluble matter when an aqueous solution of catechins is mixed with an aqueous solution of polymer A. Precipitation of the water-insoluble complex can be confirmed by turbidity of the mixture or by the presence of a peak originating from the water-insoluble complex when the mixture is measured with a laser diffraction/scattering particle size distribution analyzer.

The polymer A includes polyvinyl pyrrolidone, polyvinyl alcohol, and hydroxyethyl cellulose, among which polyvinyl pyrrolidone (hereinafter abbreviated sometimes as PVP) is preferable.

From the viewpoint of effectively suppressing coloration of catechins, the weight-average molecular weight of polymer A is preferably 6000 or more, more preferably 60000 or more, even more preferably 400000 or more, even more preferably 1300000 or more. The molecular weight is preferably 3000000 or less, more preferably 2000000 or less, from the viewpoint of obtaining a fine water-insoluble complex by preventing the water-insoluble complex from forming clumpy aggregates.

In the present invention, the weight-average molecular weight of polymer A is a value determined for example by a laser diffraction scattering method that is a general weight-average molecular weight measuring method.

In the method of the present invention, the amount of polymer A added is preferably 1 to 4 times, more preferably 1 to 3 times, even more preferably 1.2 to 2.2 times, the weight of the catechins, from the viewpoint of effectively suppressing coloration of catechins.

In the present invention, an aqueous solution of polymer A, etc. are added to an aqueous solution of catechins, etc. and mixed by means of a stirrer or the like, thereby forming a water-insoluble complex to suppress coloration of the catechins.

The hydrogel particles of the present invention contain a water-insoluble complex of catechins and polymer A.

The "hydrogel" referred to in the present invention refers to a water-containing swollen body of a water-insoluble polymer (gel former) formed with water as a solvent. The gel former is preferably a naturally occurring polymer compound and includes, for example, seaweed extracts such as agar, κ-carrageenan, ι-carrageenan, λ-carrageenan, furcelleran, alginate, and propylene glycol alginate; plant seed viscous substances such as guar gum, locust bean gum, tamarind seed polysaccharides, tara gum, and quassia gum; plant fruit viscous substances such as pectin and arabinogalactan; viscous substances produced by microorganisms, such as xanthan gum, scleroglucan, pullulan, dextran, gellan gum and curdlan; animal proteins such as gelatin, albumin and casein; vegetable proteins such as soy protein and wheat protein; cellulose and derivatives thereof, such as carboxymethyl cellulose, methyl cellulose and microcrystalline cellulose; and starch and derivatives thereof, such as starch phosphate and starch glycolate. These gel formers may be used singly or as a mixture of two or more thereof. κ-Carrageenan, agar and gellan gum are preferable as polymers that form physically collapse-prone, brittle gel particles.

The dissolution temperature of agar in water is generally 75° C. or more, mainly 75 to 90° C., and when agar is dissolved in water and then cooled, the gelling temperature is 30 to 45° C.

The water-insoluble complex of catechins and polymer A is dispersed in a continuous phase containing a gel former and water and included in the hydrogel particles of the present invention. In the water-insoluble complex, the amount of polymer A is preferably 1 to 4 times, more preferably 1 to 3 times, even more preferably 1.2 to 2.2 times, the weight of the catechins, from the viewpoint of effectively suppressing the coloration of catechins.

The content of the water-insoluble complex of catechins and polymer A in the hydrogel particles of the present invention is preferably 12% by weight or less, more preferably 8% by weight or less, even more preferably 6% by weight or less, from the viewpoint of obtaining a fine water-insoluble complex by preventing the water-insoluble complex from forming clumpy aggregates.

The content of the gel former in the hydrogel particles of the present invention is preferably 0.25 to 5.0% by weight, more preferably 0.5 to 4.0% by weight, even more preferably 1.0 to 3.0% by weight, from the viewpoint of preventing the hydrogel particles from collapsing upon incorporation into another preparation.

The hydrogel particles of the present invention may contain water-soluble organic compounds such as sugars and polyhydric alcohols and components such as a colorant, a preservative and a water-soluble perfume in addition to the water-insoluble complex of the present invention, the gel former, and water.

The sugars include glucose, galactose, fructose, mannose, mannitol, saccharose, maltose, and lactose.

The polyhydric alcohols include glycerin, sorbitol, ethylene glycol, polyethylene glycol, propylene glycol, polypropylene glycol, and oligosaccharide.

From the viewpoint of outward appearance and productivity, the average particle size of the hydrogel particles of the present invention is preferably 5 to 10000 μm, more preferably 100 to 10000 μm, even more preferably 200 to 5000 μm. The average particle size of the hydrogel particles is expressed in weight average particle size that is determined by subjecting 100 g of the particles to wet classification in water by using sieves with various mesh screens and then removing excess water therefrom with filter paper (sieve method).

The shape of the hydrogel particle of the present invention is not particularly limited, but is preferably the shape of a body of revolution which is composed of a curved surface. The "body of revolution which is composed of a curved surface" refers to a three-dimensional body defined by rotating a closed plane formed by a continuous curve and a virtual axis, but does not include a three-dimensional body having a flat surface, such as a triangular pyramid, circular cylinder, etc. In view of beautiful appearance, the shape of the hydrogel particle is more preferably spherical or elliptical.

The process for producing the hydrogel particles of the present invention is not particularly limited. For example, a gel former such as agar and polymer A are mixed with deionized water and then dissolved sufficiently by heating at a temperature higher than the dissolution temperature. An aqueous solution of catechins is added to, and mixed with, the mixture and then subjected to a general dropping, spraying or stirring method to yield hydrogel particles.

The dropping method utilizes such a property of the mixture as to form droplets by its surface or interfacial tension upon ejection through an orifice. The droplets are cooled in a gaseous phase (e.g., air) or liquid phase to solidify into hydrogel particles. In view of producing hydrogel particles of uniform particle diameter, the mixture ejected through an orifice is preferably vibrated.

The spraying method uses a spray nozzle through which the mixture is sprayed into a gaseous phase such that droplets of the mixture are formed by the surface tension. The droplets are cooled in the gaseous phase to solidify into hydrogel particles.

In the stirring method, the mixture is poured into a solution which has a property of being substantially unmixable with the mixture and which is regulated to a temperature equal to or higher than the gelation temperature. The solution is stirred such that the mixture is atomized by the shearing force of stirring, whereby droplets are formed by the surface tension. The droplets are cooled in a liquid which is substantially unmixable with the mixture to solidify into hydrogel particles.

Whichever of the dropping method, spraying method, and stirring method employed, the temperature of the mixture when ejected, sprayed, or poured is preferably between the gelation temperature and 100° C. In view of readily producing spherical particles with a beautiful appearance, the temperature of the oil-in-water dispersion is preferably higher than the gelation temperature by 10° C. or more, more preferably higher than the gelation temperature by 20° C. or more. It should be noted that the upper limit of this temperature is the boiling point of water, i.e., 100° C.

The hydrogel of the present invention can be incorporated into cosmetics, detergents, bath agents, etc. The hydrogel can also be incorporated into an oral composition, particularly a dentifrice composition.

The hydrogel particles contained in the dentifrice composition of the present invention contain the catechins and a water-soluble polymer (hereinafter referred to polymer A) forming a water-insoluble complex with the catechins.

In the description, the "hydrogel" refers to a water-containing swollen body of a water-insoluble polymer (gel former) with water as solvent, and the gel former is preferably a naturally occurring polymer compound.

The content of catechins in the hydrogel particles of the present invention is preferably 0.001 to 10% by mass, more preferably 0.001 to 6% by mass, even more preferably 0.01 to 2% by mass, from the viewpoint of the efficient action of catechins on gums and of the stability of hydrogel particles. From the viewpoint of effectively suppressing coloration of catechins, the content of polymer A is preferably 1 to 4 times, more preferably 1 to 3 times, even more preferably 1.2 to 2.2 times, the mass of the catechins.

The content of the water-insoluble complex in the hydrogel particles is preferably 12% by mass or less, more preferably 8% by mass or less, even more preferably 6% by mass or less, from the viewpoint of obtaining a fine water-insoluble complex by suppressing the water-insoluble complex from forming clumpy aggregates.

In the present invention, the gel former used in the hydrogel particles is as described above.

The content of the gel former in the hydrogel particles of the present invention is as described above, from the viewpoint of preventing the hydrogel particles from collapsing upon incorporation into a dentifrice composition.

The hydrogel particles of the present invention may contain water-soluble organic compounds such as sugars and polyhydric alcohols and components such as a colorant, a preservative and a water-soluble perfume as described above, in addition to catechins, polymer A, the gel former and water.

The process for producing the hydrogel particles of the present invention is as described above.

[Dentifrice Composition]

The dentifrice composition of the present invention contains the hydrogel particles described above, a binder and water.

The binder used in the present invention includes, for example, sodium alginate, carboxymethylcellulose sodium, carrageenan, xanthan gum, sodium polyacrylate, hydroxyethyl cellulose, hydroxypropyl cellulose, pectin, tragacanth gum, gum arabic, guar gum, karaya gum, locust bean gum, gellan gum, tamarind gum, psyllium seed gum, polyvinyl alcohol, sodium chondroitin sulfate, and a methoxy ethylene-maleic anhydride copolymer, among which sodium alginate, carboxymethylcellulose sodium, carrageenan, and xanthan gum are preferable.

Among these binders, sodium alginate is preferably one having an intramolecular mannuronic acid/guluronic acid ratio (M/G ratio) of 0.5 to 2.5, which is easily available commercially from Kimica corporation and Dainippon Pharmaceutical Co., Ltd. Carboxymethylcellulose sodium is preferably one having an etherification degree of 0.6 to 2.5, which is easily available commercially from Daicel Chemical Industries, Ltd. and Dai-ichi Kogyo Seiyaku Co., Ltd., more preferably one having an etherification degree of 0.8 to 1.5. Carrageenan that can be used may be any of 3 isomers (κ-, λ- and ι-carrageenans) and is easily and commercially available from Kelco Co., Ltd., MRC Polysaccharide co., Ltd., Taiyo Kagaku Co., Ltd., etc., more preferably ι- or λ-carrageenan. Xanthan gum that can be used is commercially available from Taiyo Kagaku Co., Ltd., Kelco Co., Ltd., Dainippon Pharmaceutical Co., Ltd. etc., and when used in combination with carboxymethyl cellulose, is preferably xanthan gum with low cellulase activity from which a small amount of contaminating cellulase was removed.

The binders may be used singly or as a mixture of two or more thereof, and the content of the binder in the composition is preferably 0.1 to 3% by mass, more preferably 0.1 to 2% by mass, even more preferably 0.2 to 1.2% by mass, from the viewpoint of attaining storage stability, the viscosity of the composition, and higher pleasant cooling sensation.

The content of the hydrogel particles in the dentifrice composition of the present invention is preferably 0.01 to 15% by mass, more preferably 0.1 to 10% by mass, even more preferably 1 to 5% by mass, from the stability of the dentifrice composition.

The amount of water in the dentifrice composition of the present invention is preferably 1 to 50% by mass, more preferably 5 to 40% by mass, even more preferably 10 to 30% by mass, from the viewpoint of attaining storage stability and higher pleasant cooling sensation.

The dentifrice composition of the present invention can further be compounded with powdery or granular erythritol having a particle size of less than 355 μm, from the viewpoint of pleasant cooling sensation and taste. In the structure of erythritol, there occurs 3 types of isomers that are L-erythritol, D-erythritol and meso-erythritol, and any of these structures can be used in the present invention. Erythritol that can be used may be an ordinarily available one and includes, for example, crystalline erythritol obtained by fermenting glucose and re-crystallizing the product. The crystalline erythritol is available as commercial products from Nikken Chemicals Co., Ltd., Mitsubishi-Kagaku Foods Corporation, Celestare, etc. Erythritol having a large particle size may be used after regulation of particle size by pulverization. For pulverization of erythritol, a roller mill, a hammer mill, a high-speed grinder or a pulverizer is generally used, among which a high-speed grinder or a hammer mill excellent in production efficiency with easy regulation of particle size is preferably used in pulverization.

The particle size of erythritol is preferably 45 μm or more to less than 355 μm, more preferably 53 μm or more to less than 300 μm, even more preferably 75 μm or more to less than 250 μm, from the viewpoint of long-lasting pleasant cooling sensation in the mouth. Erythritol having a particle size of 45 μm or more is preferable because the pleasant cooling sensation is long-lasting without instantaneous dissolution in the mouth. Erythritol having a particle size of less than 355 μm is readily dissolved in the mouth and can demonstrate a pleasant cooling sensation.

The particle size of erythritol is measured in the following manner.

Sieve: JIS standard sieve ϕ75 mm
Mesh sizes: Under sieves having mesh sizes of 500 μm, 355 μm, 250 μm, 180 μm, 125 μm, 90 μm and 45 μm in the direction of from upper to lower stages, respectively, a receiver is placed.
Shaker: Micro-electromagnetic shaker M-2 (Tsutsui Science Instrument Co., Ltd.)
Method: 15 g of a sample is placed on a 500-μm sieve and then classified for 5 minutes with the electromagnetic shaker. The total amount of erythritol present on sieves having mesh sizes of 250 μm, 180 μm, 125 μm, 90 μm and 45 μm is determined as the amount of erythritol having a particle size of 45 μm or more to less than 355 μm.

The amount of erythritol incorporated into the dentifrice composition of the present invention is preferably 15 to 60% by mass, more preferably 20 to 55% by mass, even more preferably 25 to 50% by mass, even more preferably 30 to 50% by mass, from the viewpoint of a pleasant cooling sensation.

Erythritol is desirably dispersed in a powdery state in the dentifrice composition. For this state, erythritol is introduced preferably in the form of powder in the final stage of production. By using such a method, erythritol is hardly dissolved in water and can be present in a powdery state in the dentifrice composition.

The dentifrice composition of the present invention may further contain an abrasive. The abrasive includes not only silica such as precipitated silica, silica gel, aluminosilicate, silconosilicate, and gluconosilicate but also calcium carbonate, calcium hydrogen phosphate, calcium pyrophosphate, aluminum hydroxide, alumina, magnesium carbonate, and magnesium phosphate. The content of the abrasive in the dentifrice composition of the present invention is preferably 0 to 15% by mass, more preferably 0 to 12% by mass.

Other compounding ingredients usable in the oral composition, for example antioxidants, wetting agents, medicinal components, foaming agents, preservatives, flavorings, sweetening agents, pH adjusters and the like may be incorporated into the dentifrice composition of the present invention in such a range that the purpose of the present invention is not hindered.

The antioxidants include components having antioxidative potency or reducing power and usable in oral compositions, for example, L-ascorbic acid and salts thereof, erythorbic acid and salts thereof, α-tocopherol acetic acid, dl-α-tocopherol, rosemary extract, stevia extract, sunflower seed extract, propyl gallate, dibutyl hydroxy toluene, butyl hydroxy anisole, L-cysteine hydrochloride, phytic acid, hydroquinone and glycosides thereof, nordihydroguaiuretic acid, ascorbic higher fatty acid esters (laurate, stearate, isostearate, palmitate etc.) and guaiac gum. Salts of L-ascorbic acid, erythorbic acid or α-tocopherol acetic acid include sodium salts, calcium salts, ferrous salts and palmitate salt. These antioxidants may be used singly or as a mixture of two or more selected antioxidants. The content of the antioxidant in the dentifrice composition of the present invention is preferably 0.0005 to 50% by mass, more preferably 0.001 to 20% by mass, even more preferably 0.01 to 5% by mass, from the viewpoint of suppressing a change in color of outside.

The wetting agents include, for example, glycerin, sorbitol, polyethylene glycol, propylene glycol, ethylene glycol, 1,3-butylene glycol, polypropylene glycol, xylitol, erythritol, maltitol and lactitol, and a combination of one or two or more thereof may be incorporated into the composition. The content of these wetting agents in the dentifrice composition of the present invention is preferably 40 to 95% by mass, more preferably 60 to 80% by mass, from the viewpoint of securing transparency.

The dentifrice composition of the present invention can be formed in a usual manner into a paste dentifrice composition, a liquid dentifrice composition, a gel-like dentifrice composition, etc. depending on its intended use.

EXAMPLES

Figure 1:
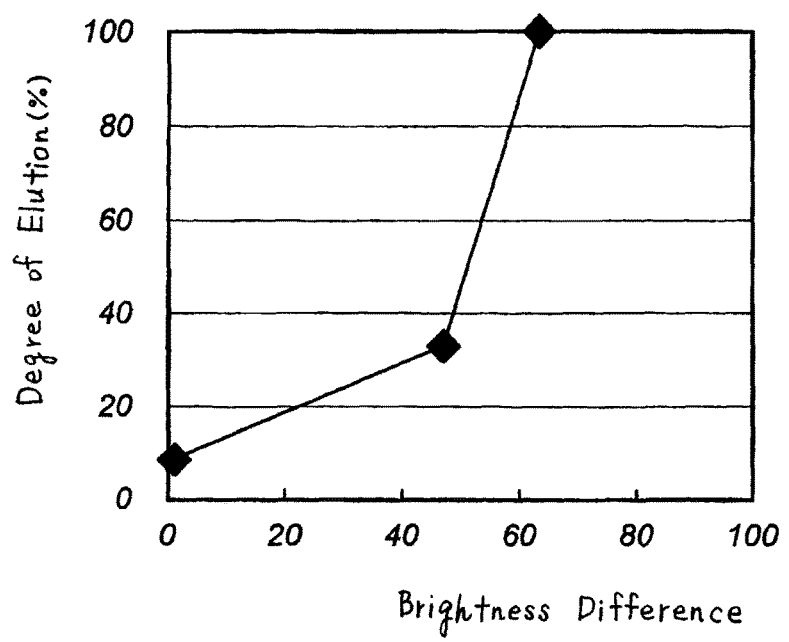
FIG. 1 is a graph showing the relationship between brightness difference obtained in Test Example 1 and the degree of elution of catechins in Test Example 2.

The following examples further describe and demonstrate embodiments of the present invention. The examples are given solely for the purpose of illustration and are not to be construed as limitations of the present invention.

In the following examples, the average particle size of hydrogel particles was measured by the sieve method described above.

Example 1

An aqueous solution (85° C.) prepared by dissolving 20 g of polyvinyl pyrrolidone (K-15, weight-average molecular weight 8000, manufactured by ISP) in 330 g of deionized water was mixed by a homomixer (8000 r/min, 1 minute) with an aqueous solution (20° C.) prepared by dissolving 10 g of catechin powder (Sunphenon 100S manufactured by Taiyo Kagaku Co., Ltd.) in 140 g of deionized water, to yield an aqueous catechin/PVP complex dispersion with the composition in Table 1.

TABLE 1

|  | % by weight |
|---|---|
| Polyvinyl pyrrolidone (K-15) | 4.0 |
| Catechin (Sunphenon 100S) | 2.0 |
| Deionized water | 94.0 |

Example 2

An aqueous solution (85° C.) prepared by dissolving 12.5 g of agar (UP-37 manufactured by Ina Food Industry Co., Ltd.), 4 g of PVP (K-30, weight-average molecular weight of 60000, manufactured by ISP) and 12 g of PVP (K-90, weight-average molecular weight of 1300000, manufactured by ISP) in 321.5 g of deionized water was mixed by a homomixer (8000 r/min, 1 minute) with an aqueous solution (20° C.) prepared by dissolving 10 g of catechin powder (Sunphenon 100S) in 140 g of deionized water, and then sprayed into a gaseous phase to yield catechin/PVP complex-included hydrogel particles with the composition in Table 2. The average particle size of the hydrogel particles was 195 μm.

TABLE 2

|  | % by weight |
|---|---|
| Agar (UP-37) | 2.5 |
| Polyvinyl pyrrolidone (K-30) | 0.8 |
| Polyvinyl pyrrolidone (K-90) | 2.4 |
| Catechin (Sunphenon 100S) | 2.0 |
| Deionized water | 92.3 |

Comparative Example 1

10 g of catechin powder (Sunphenon 100S) was dissolved in 490 g of deionized water to prepare a 2 wt % aqueous catechin solution.

Test Example 1

The aqueous catechin/PVP complex dispersion obtained in Example 1, the catechin/PVP complex-included hydrogel particles in Example 2 and the aqueous catechin solution in Comparative Example 1 were used to prepare preparations with the compositions shown in Table 3. The resulting preparations were stored at 50° C. for 1 month and measured for brightness difference before and after storage, and by this brightness difference, the degree of discoloration was evaluated. The results are shown in Table 3.

<Method of Measuring the Brightness Difference>

A transparent case with an internal size of 3 cm×3 cm×1 cm (PS CASE No. 1, manufactured by AS ONE) was filled up with the preparation after storage. Together with the case, nine points in KODAK GRAY SCALE, that is, A, 2, 4, 6, 8, 10, 12, 14 and B (assumed to be color densities 1 to 9, respectively) as color density standards, and CASMATCH (manufactured by Dai Nippon Printing Co., Ltd.), were photographed on a white paper in the same visual field. The photographing was conducted at a constant shutter speed, stop and focal distance under uniform lighting with a ring light. The photographed image was color-corrected with CASMATCH in an ADOBE PHOTOSHOP, then the brightness (brightness in HSB color model) in a site to be measured was quantified with WINROOF (Mitani Corporation), and the difference between the brightness of the sample stored at 50° C. for 1 month and the initial brightness was determined as the degree of discoloration by using the following equation:

Degree of discoloration=(brightness after storage at 50° C. for 1 month)−(initial brightness)

TABLE 3

|  |  | Test No. | | |
|---|---|---|---|---|
|  |  | 1-1 | 1-2 | 1-3 |
| Composition (% by weight) | Polyethylene glycol 600[1] | 4.0 | 4.0 | 4.0 |
|  | Sodium fluoride | 0.2 | 0.2 | 0.2 |
|  | Sorbit Liquid(70% aqueous solution) | 40.0 | 40.0 | 40.0 |
|  | Silicic anhydride | 15.0 | 15.0 | 15.0 |
|  | Sodium lauryl sulfate | 1.0 | 1.0 | 1.0 |
|  | Carboxymethylcellulose sodium[2] | 0.5 | 0.5 | 0.5 |
|  | DL-malic acid | 0.1 | 0.1 | 0.1 |
|  | Ascorbic acid | 0.1 | 0.1 | 0.1 |
|  | Anhydrous sodium pyrophosphate | 0.2 | 0.2 | 0.2 |
|  | Saccharine sodium | 0.1 | 0.1 | 0.1 |
|  | Perfume | 1.0 | 1.0 | 1.0 |
|  | Colorant | trace amount | trace amount | trace amount |
|  | Aqueous catechin/PVP complex dispersion in Example 1 | 3.0 |  |  |
|  | Catechin/PVP complex-including hydrogel particles in Example 2 |  | 3.0 |  |
|  | Aqueous catechin solution in Comparative example 1 |  |  | 3.0 |
|  | Deionized water | Balance | Balance | Balance |
| Brightness difference |  | 46.9 | 1.2 | 63.4 |

[1]Polyethylene glycol with an average molecular weight of 600
[2]CMC<1150> manufactured by Daicel Chemical Industries, Ltd.

As is evident from Table 3, discoloration is more suppressed when the aqueous catechin/PVP complex dispersion in Example 1 or the catechin/PVP complex-included hydrogel particles in Example 2 was incorporated than when the aqueous catechin solution in Comparative Example 1 was incorporated, and particularly coloration is significantly suppressed when the hydrogel particles in Example 2 is incorporated. Accordingly, it can be seen that in the aqueous catechin/PVP complex dispersion in Example 1 or in the catechin/PVP complex-included hydrogel particles in Example 2, catechins are suppressed from discoloring by oxidation and/or polymerization, thereby stabilizing catechins.

Test Example 2

The aqueous catechin/PVP complex dispersion obtained in Example 1, the catechin/PVP complex-included hydrogel particles in Example 2, and the aqueous catechin solution in Comparative Example 1 were used to prepare aqueous sodium lauryl sulfate solutions with the compositions shown in Table 4. The amount of catechin eluted into the aqueous sodium lauryl sulfate solution after 1 month of storage at room temperature was quantified by the following method to determine the degree of elution. The results are shown in Table 4.

<Method of Quantifying the Concentration of Catechin in the Aqueous Sodium Lauryl Sulfate Solution>

1.0 g of the sample (aqueous sodium lauryl sulfate solution) is taken and then mixed with 19.0 g phosphate buffer and 5.0 g iron tartrate reagent. The absorbance of the prepared mixture at 540 nm is measured. Separately, aqueous catechin solutions of known concentration are prepared from catechin powder (Sunphenon 100S) and used to prepare a calibration curve. The concentration of catechin in the sample is determined from the calibration curve to determine the degree of elution. The iron tartrate reagent is prepared by dissolving 100 mg ferrous sulfate ($7H_2O$) and 500 mg sodium potassium tartrate in water to prepare a 100 ml solution. The phosphate buffer is prepared by mixing M/15 disodium hydrogenphosphate and M/15 dipotassium hydrogenphosphate at a ratio of 84:16.

TABLE 4

| | | Test No. | | |
|---|---|---|---|---|
| | | 2-1 | 2-2 | 2-3 |
| Composition of aqueous solution (% by weight) | Deionized water | 49.0 | 49.0 | 49.0 |
| | Ethanol | 10.0 | 10.0 | 10.0 |
| | Sodium laurate | 1.0 | 1.0 | 1.0 |
| | Aqueous catechin/PVP complex dispersion in Example 1 | 40.0 | | |
| | Catechin/PVP complex-including hydrogel particles in Example 2 | | 40.0 | |
| | Aqueous catechin solution in Comparative example 1 | | | 40.0 |
| Degree of elution (%) | | 33.0 | 8.5 | 100 |

The measurement results of brightness difference in Test Example 1 are plotted against the degree of elution of catechin obtained in Test Example 2, to show the relationship between the degree of elution and the brightness difference in FIG. 1. From FIG. 1, it was found that as the degree of elution into the aqueous sodium lauryl sulfate solution decreases, the brightness difference decreases. That is, it was found that the effect of suppressing discoloration increases with a decreasing degree of catechin into the aqueous sodium lauryl sulfate solution when the PVP/catechin complex is mixed with the aqueous sodium lauryl sulfate solution, and the oxidation and/or polymerization of catechin can be suppressed and the stability of catechin is high.

Example 3

An aqueous solution (85° C.) prepared by dissolving 12.5 g of agar (UP-37) and 10.0 g of PVP (K-30, weight-average molecular weight of 60000) in 327.5 g of deionized water was mixed by a homomixer (8000 r/min, 1 minute) with an aqueous solution (20° C.) prepared by dissolving 5 g of catechin powder (Sunphenon 100S) in 145 g of deionized water, and then sprayed into a gaseous phase to yield catechin/PVP complex-included hydrogel particles having the composition and average particle size shown in Table 5.

Example 4

Catechin/PVP complex-included hydrogel particles having the composition and average particle size shown in Table 5 were obtained in the same manner as in Example 3 except that 10.0 g of PVP (K-60, weight-average molecular weight of 400000, manufactured by ISP) was used.

Example 5

Catechin/PVP complex-included hydrogel particles having the composition and average particle size shown in Table 5 were obtained in the same manner as in Example 3 except that 10.0 g of PVP (K-90, weight-average molecular weight of 1300000) was used.

TABLE 5

| | | Example 3 | Example 4 | Example 5 |
|---|---|---|---|---|
| Hydrogel particles (% by weight) | Agar (UP-37) | 2.5 | 2.5 | 2.5 |
| | Polyvinyl pyrrolidone (K-30) | 2.0 | | |
| | Polyvinyl pyrrolidone (K-60) | | 2.0 | |
| | Polyvinyl pyrrolidone (K-90) | | | 2.0 |
| | Catechin (Sunphenon 100S) | 1.0 | 1.0 | 1.0 |
| | Deionized water | 94.5 | 94.5 | 94.5 |
| Average particle diameter (μm) | | 210 | 200 | 205 |

Test Example 3

The catechin/PVP complex-included hydrogel particles prepared in Examples 3 to 5 were used to prepare aqueous sodium lauryl sulfate solutions with the compositions shown in Table 6. The amount of catechin eluted into the sodium lauryl sulfate solution after 10 days of storage at room temperature was quantified in the same manner as in Test Example 2 to determine the degree of elution. The results are shown in Table 6.

TABLE 6

| | | Test No. | | |
|---|---|---|---|---|
| | | 3-1 | 3-2 | 3-3 |
| Composition of aqueous solution (% by weight) | Deionized water | 49.0 | 49.0 | 49.0 |
| | Ethanol | 10.0 | 10.0 | 10.0 |
| | Sodium laurate | 1.0 | 1.0 | 1.0 |
| | Catechin/PVP complex-including hydrogel particles in Example 3 | 40.0 | | |

TABLE 6-continued

|  | Test No. | | |
|---|---|---|---|
|  | 3-1 | 3-2 | 3-3 |
| Catechin/PVP complex-including hydrogel particles in Example 4 |  | 40.0 |  |
| Catechin/PVP complex-including hydrogel particles in Example 5 |  |  | 40.0 |
| Degree of elution (%) | 46.0 | 37.0 | 28.5 |

From the results in Table 6, it can be seen that as the molecular weight of PVP in the hydrogel particles increases, the degree of elution into the aqueous sodium lauryl sulfate can be reduced. When the relationship with the brightness difference in Test Example 1 is utilized, it was found that the effect of suppressing discoloration increases with an increasing molecular weight of PVP, the oxidation and/or polymerization of catechin can be suppressed, and the stability of catechin is high.

Example 6

An aqueous solution (85° C.) prepared by dissolving 12.5 g of agar (UP-37), 3.0 g of PVP (K-30) and 9.0 g of PVP (K-90) in 325.5 g of deionized water was mixed by a homomixer (8000 r/min, 1 minute) with an aqueous solution (20° C.) prepared by dissolving 10 g catechin powder (Sunphenon 100S) in 140 g of deionized water, and then sprayed into a gaseous phase to yield catechin/PVP complex-included hydrogel particles having the composition and average particle size shown in Table 7.

Example 7

An aqueous solution (85° C.) prepared by dissolving 12.5 g of agar (UP-37), 3.5 g of PVP (K-30) and 10.5 g of PVP (K-90) in 323.5 g of deionized water was mixed by a homomixer (8000 r/min, 1 minute) with an aqueous solution (20° C.) prepared by dissolving 10 g of catechin powder (Sunphenon 100S) in 140 g of deionized water, and then sprayed into a gaseous phase to yield catechin/PVP complex-included hydrogel particles having the composition and average particle size shown in Table 7.

Example 8

An aqueous solution (85° C.) prepared by dissolving 12.5 g of agar (UP-37), 5.0 g of PVP (K-30) and 15.0 g of PVP (K-90) in 323.5 g of deionized water was mixed by a homomixer (8000 r/min, 1 minute) with an aqueous solution (20° C.) prepared by dissolving 10 g of catechin powder (Sunphenon 100S) in 140 g of deionized water, and then sprayed into a gaseous phase to yield catechin/PVP complex-included hydrogel particles having the composition and average particle size shown in Table 7.

Example 9

An aqueous solution (85° C.) prepared by dissolving 12.5 g of agar (UP-37), 5.5 g of PVP (K-30) and 16.5 g of PVP (K-90) in 323.5 g of deionized water was mixed by a homomixer (8000 r/min, 1 minute) with an aqueous solution (20° C.) prepared by dissolving 10 g of catechin powder (Sunphenon 100S) in 140 g of deionized water, and then sprayed into a gaseous phase to yield catechin/PVP complex-included hydrogel particles having the composition and average particle size shown in Table 7.

TABLE 7

|  |  | Example 6 | Example 7 | Example 8 | Example 9 |
|---|---|---|---|---|---|
| Hydrogel particles (% by weight) | Agar (UP-37) | 2.5 | 2.5 | 2.5 | 2.5 |
|  | Polyvinyl pyrrolidone (K-30) | 0.6 | 0.7 | 1.0 | 1.1 |
|  | Polyvinyl pyrrolidone (K-90) | 1.8 | 2.1 | 3.0 | 3.3 |
|  | Catechin (Sunphenon 100S) | 2.0 | 2.0 | 2.0 | 2.0 |
|  | Deionized water | 93.1 | 92.7 | 91.5 | 91.1 |
| Weight ratio of catechin/PVP |  | 1/1.2 | 1/1.4 | 1/2.0 | 1/2.2 |
| Average particle diameter (μm) |  | 215 | 230 | 210 | 220 |

Test Example 4

The catechin/PVP complex-included hydrogel particles prepared in Example 2 and Examples 6 to 9 were used to prepare aqueous sodium lauryl sulfate solutions with the compositions shown in Table 8. The amount of catechin eluted into the aqueous sodium lauryl sulfate solution after 20 days of storage at room temperature was quantified in the same manner as in Test Example 2 to determine the degree of elution. The results are shown in Table 8.

TABLE 8

|  |  | Test No. | | | | |
|---|---|---|---|---|---|---|
|  |  | 4-1 | 4-2 | 4-3 | 4-4 | 4-5 |
| Composition of aqueous solution (% by weight) | Deionized water | 49.0 | 49.0 | 49.0 | 49.0 | 49.0 |
|  | Ethanol | 10.0 | 10.0 | 10.0 | 10.0 | 10.0 |
|  | Sodium laurate | 1.0 | 1.0 | 1.0 | 1.0 | 1.0 |
|  | Catechin/PVP complex-including hydrogel particles in Example 2 | 40.0 |  |  |  |  |
|  | Catechin/PVP complex-including hydrogel particles in Example 6 |  | 40.0 |  |  |  |
|  | Catechin/PVP complex-including hydrogel particles in Example 7 |  |  | 40.0 |  |  |
|  | Catechin/PVP complex-including hydrogel particles in Example 8 |  |  |  | 40.0 |  |
|  | Catechin/PVP complex-including hydrogel particles in Example 9 |  |  |  |  | 40.0 |
| Catechin/PVP weight ratio in hydrogel particles |  | 1/1.6 | 1/1.2 | 1/1.4 | 1/2.0 | 1/2.2 |
| Degree of elution (%) |  | 8.5 | 14.0 | 10.0 | 22.0 | 30.0 |

As is evident from Table 8, it can be seen that when hydrogel particles with a catechin/PVP weight ratio of 1.0/1.6 was incorporated, the degree of elution is the minimum. That is, it was found that when the catechin/PVP weight ratio in the hydrogel particles is 1.0/1.6, the effect of suppressing discoloration is the highest, the coloration of catechin can be suppressed and the stability of catechin is high.

The dentifrice composition of the present invention will be described by reference to the following examples.

In the Examples, "%" refers to "% by mass" unless otherwise specified.

Production Example 1

An aqueous solution (85° C.) prepared by dissolving 15 g of agar (UP-37 manufactured by Ina Food Industry Co., Ltd.) and 16 g of PVP (K-90, weight-average molecular weight of 1300000, manufactured by ISP) in 319 g of deionized water was mixed by a homomixer (8000 r/min, 1 minute) with an aqueous solution (20° C.) prepared by dissolving 10 g of tea extract (Sunphenon 100S, catechin content 60 to 70%, manufactured by Taiyo Kagaku Co., Ltd.) in 140 g of deionized water, and then sprayed into a gaseous phase to yield hydrogel particles with the composition shown in Table 9. The average particle size of the hydrogel particles was 200 μm.

TABLE 9

| Composition of hydrogel particles | |
|---|---|
| Compound name | Proportion (%) |
| Tea extract (catechin content 60 to 70%) | 2 |
| Agar | 3 |
| PVP | 3.2 |
| Purified water | Balance |
| Total | 100 |

Example 10

Figure 2:
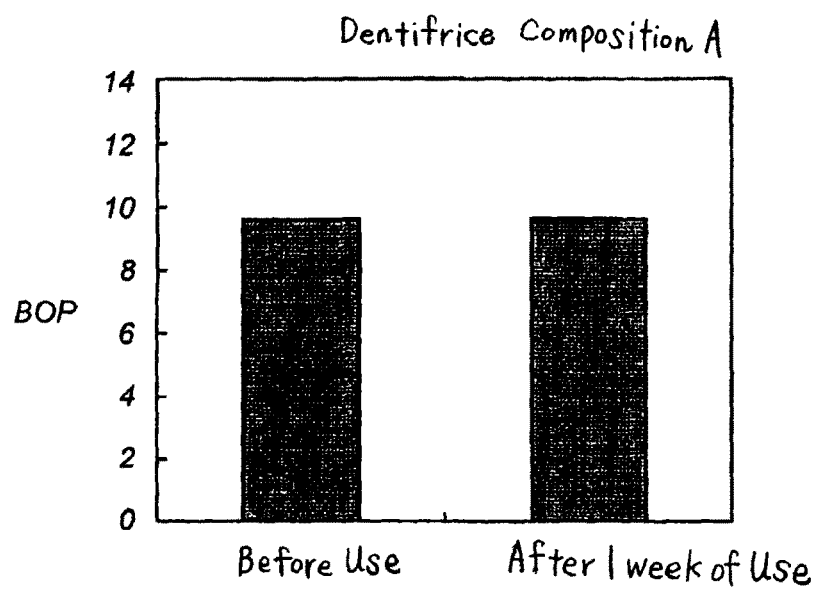
FIG. 2 is a graph showing the effect of dentifrice composition A on the gum.
Figure 3:
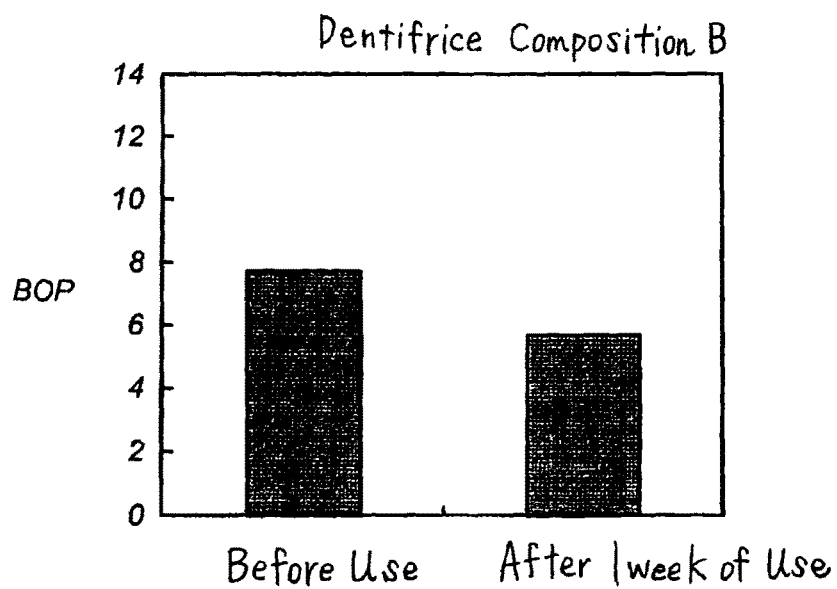
FIG. 3 is a graph showing the effect of dentifrice composition B on the gum.

The hydrogel particles obtained in Production Example 1 or the tea extract (Sunphenon 100S, catechin content 60 to 70%, manufactured by Taiyo Kagaku Co., Ltd.) was used to prepare dentifrice composition A (Comparative Product) and dentifrice composition B (Invented Product) having the compositions shown in Table 10. The resulting dentifrice compositions A and B were evaluated for their discoloration and taste by the following methods. The results are shown in Table 10. The effect on the gum was also examined by the following method. The results are shown in FIGS. 2 and 3.

<Method of Evaluating Discoloration>

The resulting dentifrice composition was filled in a container, stored at 50° C. for 1 month, and measured for brightness difference after storage by the following method, and by this brightness difference, the degree of discoloration was evaluated. A transparent case with an internal size of 3 cm×3 cm×1 cm (PS CASE No. 1, manufactured by AS ONE) was filled up with the dentifrice preparation after storage. Together with the case, nine points in KODAK GRAY SCALE, that is, A, 2, 4, 6, 8, 10, 12, 14 and B (assumed to be color densities 1 to 9, respectively) as color density standards, and CASMATCH (manufactured by Dai Nippon Printing Co., Ltd.), were photographed on white paper in the same visual field. The photographing was conducted at a constant shutter speed, stop and focal distance under uniform lighting with a ring light. The photographed image was color-corrected with CASMATCH in an ADOBE PHOTOSHOP, then the brightness (brightness in HSB color model) in a site to be measured was quantified with WINROOF (Mitani Corporation), and the difference between the brightness of the sample stored at 50° C. for 1 month and the (initial) brightness just after production was determined as the degree of discoloration by using the following equation (I):

$$\text{Degree of discoloration} = (\text{brightness after storage at } 50° \text{ C. for 1 month}) - (\text{initial brightness}) \qquad (I)$$

<Method of Evaluating Taste>

Flavors of the dentifrice compositions A and B were evaluated by a panel of 9 experts under the following 3 criteria, and the results are shown in mean value.

Evaluation Criteria

1: Not astringent.

2: Not very astringent.

3: Astringent.

<Effect on the Gum>

The dentifrice compositions A and B were used respectively for 1 week by 9 male and female persons in their twenties to fifties and examined for change in BOP (Bleeding On Probing) before and after use. BOP (Bleeding On Probing) refers to a state of bleeding occurring when a WHO probe is removed after insertion into the bottom of the gum in a periodontal pocket (gap between tooth and gum). Bleeding does not occur when the gum is healthy, while bleeding easily occurs when there is inflammation in the pocket and the bottom of the gum. That is, the gum is in a worse state as the number of BOP sites increases.

TABLE 10

| | | Dentifrice composition A | Dentifrice composition B |
|---|---|---|---|
| Composition (%) | Polyethylene glycol 600*[1] | 4 | 4 |
| | Sodium fluorate | 0.2 | 0.2 |
| | Sorbit liquid(70% aqueous solution) | 40 | 40 |
| | Abrasive silica*[2] | 10 | 10 |
| | Thickening silica*[3] | 5 | 5 |
| | Sodium lauryl sulfate | 1 | 1 |
| | Carboxymethylcellulose sodium*[4] | 0.5 | 0.5 |
| | DL-malic acid | 0.1 | 0.1 |
| | Ascorbic acid | 0.1 | 0.1 |
| | Anhydrous sodium pyrophosphate | 0.2 | 0.2 |
| | Saccharine sodium | 0.1 | 0.1 |
| | Perfume | 1 | 1 |
| | Colorant | Trace amount | Trace amount |
| | Tea extract*[5] | 0.06 | — |
| | Hydrogel particles in Production example 1 | — | 3 |
| | Purified water | Balance | Balance |
| | Total | 100 | 100 |

TABLE 10-continued

|  |  | Dentifrice composition A | Dentifrice composition B |
|---|---|---|---|
| Results of evaluation | Degree of discoloration | 63.4 | 1.2 |
|  | Taste | 2.5 | 1.67 |

*[1]Polyethylene glycol with an average molecular weight of 600
*[2]Solbocyl AC43 (Ineos Silicas Limited)
*[3]Solbocyl TC15 (Ineos Silicas Limited)
*[4]CMC<1150> manufactured by Daicel Chemical Industries, Ltd.
*[5]Sunphenon 100S, catechin content 60 to 70%, manufactured by Taiyo Kagaku Co., Ltd.

As is evident from Table 10, the dentifrice composition B containing the catechin-included hydrogel particles of the present invention, as compared with the dentifrice composition A containing catechins as they are without being included, was significantly prevented from discoloring and was superior in taste.

As is evident from FIGS. 2 and 3, it can be seen that when the dentifrice composition A is used, the value of BOP is substantially not changed in 1 week, and the state of gum is not improved, while when the dentifrice composition B is used, the value of BOP is lowered in 1 week, and the state of gum is improved. It is estimated that catechins formed into hydrogel particles are useful in improving an effect of ameliorating gingivitis.

Example 11

The hydrogel particles obtained in Production Example 1 or the tea extract (Sunphenon 100S, catechin content 60 to 70%, manufactured by Taiyo Kagaku Co., Ltd.) was used to prepare dentifrice composition C (Comparative Product) and dentifrice composition D (Invented Product) having the compositions shown in Table 11. The resulting dentifrice compositions C and D were evaluated for their discoloration and taste by the same methods as in Example 10. The results are shown in Table 11.

TABLE 11

|  |  | Dentifrice composition C | Dentifrice composition D |
|---|---|---|---|
| Composition (%) | Polyethylene glycol 600*[1] | 4 | 4 |
|  | Sodium fluoride | 0.2 | 0.2 |
|  | Sorbit liquid (70% aqueous solution) | 21 | 21 |
|  | Erythritol*[6] | 23 | 23 |
|  | Abrasive silica*[2] | 10 | 10 |
|  | Thickening silica*[3] | 5 | 5 |
|  | Sodium lauryl sulfate | 1 | 1 |
|  | Carboxymethylcellulose sodium*[4] | 0.5 | 0.5 |
|  | DL-malic acid | 0.1 | 0.1 |
|  | Ascorbic acid | 0.1 | 0.1 |
|  | Anhydrous sodium pyrophosphate | 0.2 | 0.2 |
|  | Saccharine sodium | 0.1 | 0.1 |
|  | Perfume | 1 | 1 |
|  | Colorant | Trace amount | Trace amount |
|  | Tea extract*[5] | 0.06 | — |
|  | Hydrogel particles in Production example 1 | — | 3 |
|  | Purified water | Balance | Balance |
|  | Total | 100 | 100 |
| Results of evaluation | Degree of discoloration | 92.7 | 10.7 |
|  | Taste | 1.78 | 1.11 |

*[1] to *[5]are the same as in Table 10.
*[6]Erythritol having a particle-size distribution in which particles of less than 45 μm in particle size are 13% by mass, those of 45 μm or more to less than 250 μm are 82% by mass, and those of 250 μm or more to less than 355 μm are 5% by mass.

As is evident from Table 11, the dentifrice composition D containing the catechin-included hydrogel particles of the present invention, as compared with the dentifrice composition C containing catechins as they are without being included, was significantly prevented from discoloring and was superior in taste.

The invention claimed is:
1. A dentifrice composition comprising hydrogel particles (A), a binder (B) and water (C), wherein:
the hydrogel particles (A) comprise catechins (A1), a water-soluble polymer (A2) capable of forming a water-insoluble complex with catechins, a gel former (A3) and water (A4);
the polymer (A2) is selected from polyvinyl pyrrolidone, polyvinyl alcohol and hydroxyethyl cellulose;
the gel former (A3) is at least one selected from agar, κ-carrageenan, ι-carrageenan, λcarrageenan, furcelleran, alginate, propylene glycol alginate, guar gum, locust bean gum, tamarind seed polysaccharides, tara gum, quassia gum, pectin, arabinogalactan, xanthan gum, scleroglucan, pullulan, dextran, gellan gum, curdlan, gelatin, albumin, casein, soy protein, wheat protein, carboxymethyl cellulose, methyl cellulose, microcrystalline cellulose, starch, starch phosphate and starch glycolate;
the hydrogel particles (A) have an average particle size of 5 to 5000 μm;
the binder (B) is at least one selected from sodium alginate, carboxymethylcellulose sodium, carrageenan, xanthan gum, sodium polyacrylate, hydroxyethyl cellulose, hydroxypropyl cellulose, pectin, tragacanth gum, gum arabic, guar gum, karaya gum, locust bean gum, gellan gum, tamarind gum, psyllium seed gum, polyvinyl alcohol, sodium chondroitin sulfate and a methoxy ethylene-maleic anhydride copolymer;

the ratio (A2/A1) of the polymer (A2) to the catechins (A1) in the hydrogel particles (A) is 1 to 4 times by weight; and the dentifrice composition is contained in a storage container.

2. The dentifrice composition according to claim 1, wherein the amount of the gel former (A3) in the hydrogel particles (A) is 0.001 to 10% by mass.

3. The dentifrice composition according to claim 1, wherein the content of the binder (B) in the dentifrice composition is 0.1 to 3% by mass.

4. The dentifrice composition according to claim 1, wherein the content of the hydrogel particles (A) in the dentifrice composition is 0.01 to 15% by mass.

5. An oral composition comprising hydrogel particles (A) and water (C), wherein:

the hydrogel particles (A) comprise catechins (A1), a water-soluble polymer (A2) capable of forming a water-insoluble complex with catechins, a gel former (A3) and water (A4);

the polymer (A2) is selected from polyvinyl pyrrolidone, polyvinyl alcohol and hydroxyethyl cellulose;

the hydrogel particles (A) have an average particle size of 5 to 5000 μm;

the gel former (A3) is at least one selected from agar, κ-carrageenan, ι-carrageenan, λ-carrageenan, furcelleran, alginate, propylene glycol alginate, guar gum, locust bean gum, tamarind seed polysaccharides, tara gum, quassia gum, pectin, arabinogalactan, xanthan gum, scleroglucan, pullulan, dextran, gellan gum, curdlan, gelatin, albumin, casein, soy protein, wheat protein, carboxymethyl cellulose, methyl cellulose, microcrystalline cellulose, starch, starch phosphate and starch glycolate;

the ratio (A2/A1) of the polymer (A2) to the catechins (A1) in the hydrogel particles (A) is 1 to 4 times by weight; and the oral composition is contained in a storage container.

6. The oral composition according to claim 5, wherein the amount of the gel former (A3) in the hydrogel particles (A) is 0.001 to 10% by mass.

7. The oral composition according to claim 5, wherein the content of the hydrogel particles (A) in the oral composition is 0.01 to 15% by mass.

8. A method for producing an oral composition according to claim 5, comprising:

preparing an aqueous solution by dissolving a gel former (A3) and a water-soluble polymer (A2) capable of forming a water-insoluble complex with catechins in water (A4) at a temperature higher than the dissolution temperature of (A2) and not greater than 100 ° C., the polymer (A2) being selected from polyvinyl pyrrolidone, polyvinyl alcohol and hydroxyethyl cellulose;

obtaining a mixture solution by adding catechins (A1) to the aqueous solution;

obtaining hydrogel particles (A) by subjecting the mixture solution to a dropping, spraying or stirring method, the hydrogel particles (A) comprising the catechins (A1), the polymer (A2), the gel former (A3) and water (A4); and obtaining the oral composition using the hydrogel particles (A) and water (C).

9. The method for producing an oral composition according to claim 8, wherein the gel former (A3) is agar.

10. The method for producing an oral composition according to claim 8, wherein the temperature for preparing the aqueous solution by dissolving the gel former (A3) and the polymer (A2) in water (A4) is 80 to 100° C.

11. The dentifrice composition according to claim 1, wherein the ratio (A2/A1) of the polymer (A2) to the catechins (A1) in the hydrogel particles (A) is 1.2 to 2.2 times by weight.

12. The oral composition according to claim 5, wherein the ratio (A2/A1) of the polymer (A2) to the catechins (A1) in the hydrogel particles (A) is 1.2 to 2.2 times by weight.

13. The dentifrice composition according to claim 1, wherein the hydrogel particles (A) have an average particle size of 5 to 230 μm.

14. The oral composition according to claim 5, wherein the hydrogel particles (A) have an average particle size of 5 to 230 μm.

* * * * *